(12) United States Patent
Gerg et al.

(10) Patent No.: US 8,668,665 B2
(45) Date of Patent: Mar. 11, 2014

(54) SYSTEMS AND METHODS FOR POWER AND FLOW RATE CONTROL

(75) Inventors: James Gerg, Lake Forest, CA (US);
Carina R Reisin, Tustin, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 85 days.

(21) Appl. No.: 13/243,721

(22) Filed: Sep. 23, 2011

(65) Prior Publication Data

US 2012/0041360 A1    Feb. 16, 2012

Related U.S. Application Data

(62) Division of application No. 11/530,306, filed on Sep. 8, 2006.

(51) Int. Cl.
*A61M 1/00*    (2006.01)
*A61M 5/178*   (2006.01)
*A61M 31/00*   (2006.01)

(52) U.S. Cl.
USPC ............... 604/26; 604/31; 604/35; 604/67; 604/120; 604/521

(58) Field of Classification Search
USPC ......... 604/26–28, 30, 31, 35, 65–67, 73, 120, 604/121, 521
See application file for complete search history.

(56) References Cited

U.S. PATENT DOCUMENTS

| | | | |
|---|---|---|---|
| 3,920,014 A | 11/1975 | Banko | |
| 4,653,719 A | 3/1987 | Cabrera et al. | |
| 4,702,733 A | 10/1987 | Wright et al. | |
| 4,818,186 A * | 4/1989 | Pastrone et al. | 417/63 |
| 5,106,367 A | 4/1992 | Ureche et al. | |
| 5,167,620 A | 12/1992 | Ureche et al. | |
| 5,242,404 A | 9/1993 | Conley et al. | |
| 5,354,268 A * | 10/1994 | Peterson et al. | 604/35 |

(Continued)

FOREIGN PATENT DOCUMENTS

| | | |
|---|---|---|
| EP | 1382291 A2 | 1/2004 |
| WO | WO03047653 A1 | 6/2003 |

OTHER PUBLICATIONS

European Search Report for Application No. EP10153823, mailed on Apr. 19, 2010, 2 pages.

(Continued)

*Primary Examiner* — Kevin C Sirmons
*Assistant Examiner* — William Carpenter
(74) *Attorney, Agent, or Firm* — Abbott Medical Optics Inc.

(57) ABSTRACT

The invention is generally directed to systems and methods for fluid control, and more particularly to systems and methods for power and flow rate control for aspiration. In accordance with one embodiment, an aspiration system includes an aspiration line having distal and proximal ends and an aspiration port defined in the distal end; a fluid transport device operatively coupled to the proximal end of the aspiration line; and a flow restrictor operatively coupled to the aspiration line in between the fluid transport device and the aspiration port. To measure occlusion within the line, first and second pressure sensors are utilized, the first sensor being operatively coupled to the aspiration line between the port and the restrictor and the second sensor being operatively coupled to the aspiration line between the restrictor and the fluid transport device. The pressure differential between the two sensors can provide an indication of the onset, presence, and/or elimination of an occlusion.

9 Claims, 6 Drawing Sheets

(56) References Cited

U.S. PATENT DOCUMENTS

| | | |
|---|---|---|
| 5,476,448 A | 12/1995 | Urich |
| 5,487,827 A | 1/1996 | Peterson et al. |
| 5,591,127 A * | 1/1997 | Barwick et al. ............... 604/66 |
| 5,616,120 A | 4/1997 | Andrew et al. |
| 5,695,473 A | 12/1997 | Olsen |
| 5,697,898 A | 12/1997 | Devine |
| 5,700,240 A | 12/1997 | Barwick, Jr. et al. |
| 5,733,256 A * | 3/1998 | Costin ............................ 604/22 |
| 5,766,146 A | 6/1998 | Barwick, Jr. |
| 5,865,764 A | 2/1999 | Moorhead |
| 5,885,243 A | 3/1999 | Capetan et al. |
| 5,935,106 A | 8/1999 | Olsen |
| 6,159,175 A | 12/2000 | Strukel et al. |
| 6,167,588 B1 | 1/2001 | Dyson |
| 6,423,029 B1 * | 7/2002 | Elsberry ........................ 604/65 |
| 6,599,271 B1 | 7/2003 | Easley |
| 7,083,591 B2 | 8/2006 | Cionni |
| 2003/0050619 A1 * | 3/2003 | Mooijman et al. ............ 604/500 |
| 2005/0096593 A1 * | 5/2005 | Pope et al. .................... 604/122 |
| 2005/0234441 A1 | 10/2005 | Bisch et al. |
| 2005/0261628 A1 | 11/2005 | Boukhny et al. |
| 2006/0224107 A1 | 10/2006 | Claus et al. |
| 2006/0224143 A1 | 10/2006 | Claus et al. |

OTHER PUBLICATIONS

International Search Report for Application No. PCT/US2007/077634, mailed on Feb. 14, 2008, 3 pages.

International Preliminary Report on Patentability and Written Opinion for Application No. PCT/US2007/077634, mailed on Mar. 10, 2009, 8 pages.

* cited by examiner

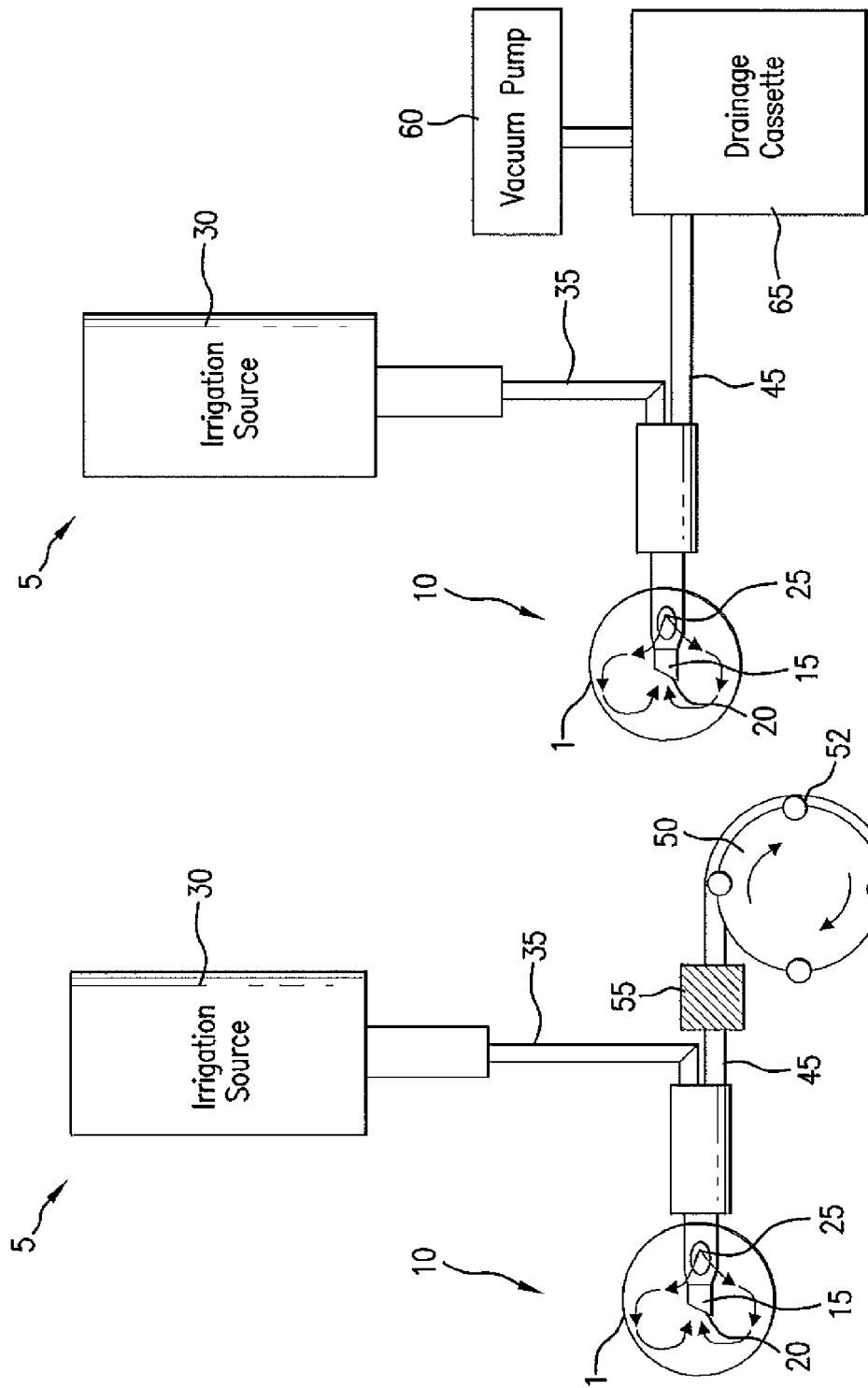

SYSTEMS AND METHODS FOR POWER AND FLOW RATE CONTROL

This application is a divisional application and claims priority to U.S. application No. 11/530,306 filed on Sep. 8, 2006, the entire contents of are hereby incorporated by reference in its entirety for all purposes as if fully set forth herein.

FIELD OF THE INVENTION

The field of the invention relates to systems and methods for fluid control, and more particularly to systems and methods for power and flow rate control.

BACKGROUND OF THE INVENTION

A number of medically recognized techniques are utilized for cataractic lens removal based on, for example, phacoemulsification, mechanical cutting or destruction, laser treatments, water jet treatments, and so on.

The phacoemulsification method includes making a corneal incision and the insertion of a phacoemulsification handpiece which includes a needle that is ultrasonically driven in order to emulsify, or liquefy, the lens. A phacoemulsification system 5 known in the art is shown in FIG. 1. The system 5 generally includes a phacoemulsification handpiece 10 coupled to an irrigation source 30 and an aspiration pump 40. The handpiece 10 includes a distal tip 15 (shown within the anterior chamber of the patient's eye 1) that emits ultrasonic energy to emulsify the cataractic lens within the patient's eye 1. The handpiece 10 further includes an irrigation port 25 proximal to the distal tip 15, which is coupled to an irrigation source 30 via an irrigation line 35, and an aspiration port 20 at the distal tip 15, which is coupled to an aspiration pump 40 via an aspiration line 45. Concomitantly with the emulsification, fluid from the irrigation source 30, which is typically an elevated bottle of saline solution, is irrigated into the eye 1 via the irrigation line 35 and the irrigation port 25, and the irrigation fluid and emulsified cataractic lens material are aspirationd from the eye 1 by the aspiration pump 40 via the aspiration port 20 and the aspiration line 45. Other medical techniques for removing cataractic lenses also typically include irrigating the eye and aspirating lens parts and other liquids. Additionally, some procedures may include irrigating the eye 1 and aspirating the irrigating fluid without concomitant destruction, alteration or removal of the lens.

Aspiration can be achieved with a variety of different aspiration pumps 40 known in the art. The two most common types are (1) volumetric flow or positive displacement pumps (such as peristaltic or scroll pumps) and (2) vacuum-based pumps (such as venturi, diaphragm, or rotary-vane pumps). Each type has its own general advantages and disadvantages. Turning to FIG. 2, an example peristaltic flow pump 50 is illustrated. In this configuration, the aspiration line 45 is in direct contact with a rotating pump head 50 having rollers 52 around its perimeter. As the pump head 50 rotates clockwise, the rollers 52 press against the line 45 causing fluid to flow within the line 45 in the direction of the rollers 52. This is referred to as a volumetric flow pump because the pump 50 directly controls the volume or rate of fluid flow. An advantage with this type of pump 50 is that the rate of fluid flow can be easily and precisely controlled by adjusting the rotational speed of the pump head 50.

Turning to FIG. 3, an example vacuum-based pump 60 is illustrated. This type of pump indirectly controls fluid flow by controlling the vacuum within the fluidic circuit. For example, the vacuum-based pump 60 can be an pneumatic pump (e.g., a venturi pump) that creates a pressure differential in a drainage cassette reservoir 65 that causes the fluid to be sucked from the aspiration line 45 into the drainage cassette reservoir 65. Thus, instead of pushing fluid through the aspiration line 45 like the flow pump 50, the fluid is essentially pulled by vacuum through the line 45. The rate of fluid flow generated by a vacuum-based pump is generally higher than the rate of fluid flow generated by a volumetric flow based pump; however, current systems and methods for controlling the rate of volumetric flow for the vacuum-based pump, which typically involve adjusting the operative vacuum level, are imprecise, which raises safety and efficacy concerns.

As is well known, for these various surgical techniques it is necessary to maintain a stable volume of liquid in the anterior chamber of the eye and this is accomplished by irrigating fluid into the eye at the same rate as aspirating fluid and lens material. For example, see U.S. Pat. No. 5,700,240, to Barwick et. al, filed Jan. 24, 1995 ("Barwick") and U.S. patent application Ser. No. 11/401,529 to Claus et. al, filed Apr. 10, 2006 ("Claus"), which are both hereby incorporated by reference in their entirety. During phacoemulsification, it is possible for the aspirating phacoemulsification handpiece 10 to become occluded. This occlusion is caused by particles blocking a lumen or tube in the aspirating handpiece 10, e.g., the aspiration port 20 or irrigation port 25. In the case of volumetric flow based pumps, this blockage can result in increased vacuum (i.e. increasingly negative pressure) in the aspiration line 45 and the longer the occlusion is in place, the greater the vacuum. In contrast, with a vacuum-based pump, this blockage can result in a volumetric fluid flow drop off near the aspiration port 20. In either case, once the occlusion is cleared, a resulting rush of fluid from the anterior chamber into the aspiration line 45 can outpace the volumetric flow of new fluid into the eye 1 from the irrigation source 30.

The resulting imbalance of incoming and outgoing fluid can create a phenomenon known as post-occlusion surge or fluidic surge, in which the structure of the anterior chamber moves rapidly as fluid is replaced due to the dynamic change in the rate of fluid flow and pressure. Such post-occlusion surge events may lead to eye trauma. The most common approach to preventing or minimizing the post-occlusion surge is to quickly adjust the vacuum-level or rate of fluid flow in the aspiration line 45 and/or the ultrasonic power of the handpiece 10 upon detection of an occlusion. Many surgeons rely on their own visual observations to detect the occlusion; however, because of the unpredictable and time-sensitive nature of the problem, a reliable computer-based detection and response system is preferable.

For current systems with volumetric flow pumps 50, if an occlusion occurs, the flow rate will decrease at the aspiration port 20 and the vacuum level within the aspiration line 45 between the pump 50 and the handpiece 10 will increase. Thus, a computer-based system (not shown) can utilize a vacuum sensor 55 placed on the aspiration line 45 to detect the vacuum increase and respond accordingly (an example of such a system is described in "Barwick" and "Claus"). For current systems with vacuum-based pumps 60, however, the vacuum level within the aspiration line 45 is tied to the vacuum power generated by the pump 60 and thus, may not be an effective indicator of whether an occlusion has occurred. Accordingly, an improved system and method for controlling the rate of fluid flow and vacuum based on the detection of occlusion within a fluid circuit is desirable.

SUMMARY OF THE INVENTION

The invention is generally directed to systems and methods for fluid control, and more particularly to systems and methods for power and flow rate control for aspiration.

In accordance with one embodiment, an aspiration system includes an aspiration line having distal and proximal ends and an aspiration port defined in the distal end; a fluid transport device operatively coupled to the proximal end of the aspiration line; and a flow restrictor operatively coupled to the aspiration line in between the fluid transport device and the aspiration port. To measure occlusion within the line, first and second pressure sensors are utilized, the first sensor being operatively coupled to the aspiration line between the port and the restrictor and the second sensor being operatively coupled to the aspiration line between the restrictor and the fluid transport device. The pressure differential between the two sensors can provide an indication of the onset, presence, and/or elimination of an occlusion.

In accordance with another embodiment, the flow restrictor is a variable flow restrictor controllable by a computer processor.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

In order to better appreciate how the above-recited and other advantages and objects of the inventions are obtained, a more particular description of the embodiments briefly described above will be rendered by reference to specific embodiments thereof, which are illustrated in the accompanying drawings. It should be noted that the components in the figures are not necessarily to scale, emphasis instead being placed upon illustrating the principles of the invention. Moreover, in the figures, like reference numerals designate corresponding parts throughout the different views. However, like parts do not always have like reference numerals. Moreover, all illustrations are intended to convey concepts, where relative sizes, shapes and other detailed attributes may be illustrated schematically rather than literally or precisely.

FIG. 2 is a diagram of a phacoemulsification system having a flow pump known in the art.

FIG. 3 is a diagram of a phacoemulsification system having a vacuum-based pump known in the art.

DETAILED DESCRIPTION OF THE PREFERRED EMBODIMENTS

What are described below are preferred embodiments of aspiration systems using vacuum-based pumps, which can be applied to any system, medical (such as phacoemulsification, wound drainage, blood circulation, dialysis, or similar), or non-medical.

Variable Flow Restrictors

In general, the rate of fluid flow is a function of three (3) basic parameters: (1) the effective viscosity of the fluid, (2) the operative or driving vacuum level, and (3) the instantaneous effective resistance of the fluid transport pathway (e.g., aspiration line 45). For many surgical procedures, a constant effective viscosity can be assumed (particularly if the fluid is predominantly a known irrigation source), and further, the operative or driving vacuum level can be easily measured and adjusted in an open-loop pressure monitoring system; however, for current aspiration systems with vacuum based pumps, the instantaneous effective resistance of the fluid transport pathway is a parameter that can vary independent of the vacuum-level, and thus, is not easily quantified or dynamically compensated for in cases such as fluid transport pathway obstruction (e.g., occlusion), which is a significant reason why volumetric flow rate is difficult to control by only adjusting the operative vacuum-level.

To compensate for the third parameter, one existing approach is to utilize a fixed flow restrictor (not shown) on the aspiration line 45 between the aspiration port 20 and the pump 60. The fixed flow restrictor can be an orifice within the line 45 that reduces the cross-sectional area of the portion of the line 45 having the orifice. This, in turn, increases the instantaneous effective resistance of the line 45 and reduces the volumetric flow rate. These fixed flow restrictors typically drop the volumetric flow rate down to rates generated by flow pumps 50, which can create a safer operating environment for surgeons (e.g., suppress post-occlusion surge), but these fixed flow restrictors also undesirably limit the range of operation that a vacuum-based pump can provide (e.g., range of allowable volumetric flow rates).

Figure 1:
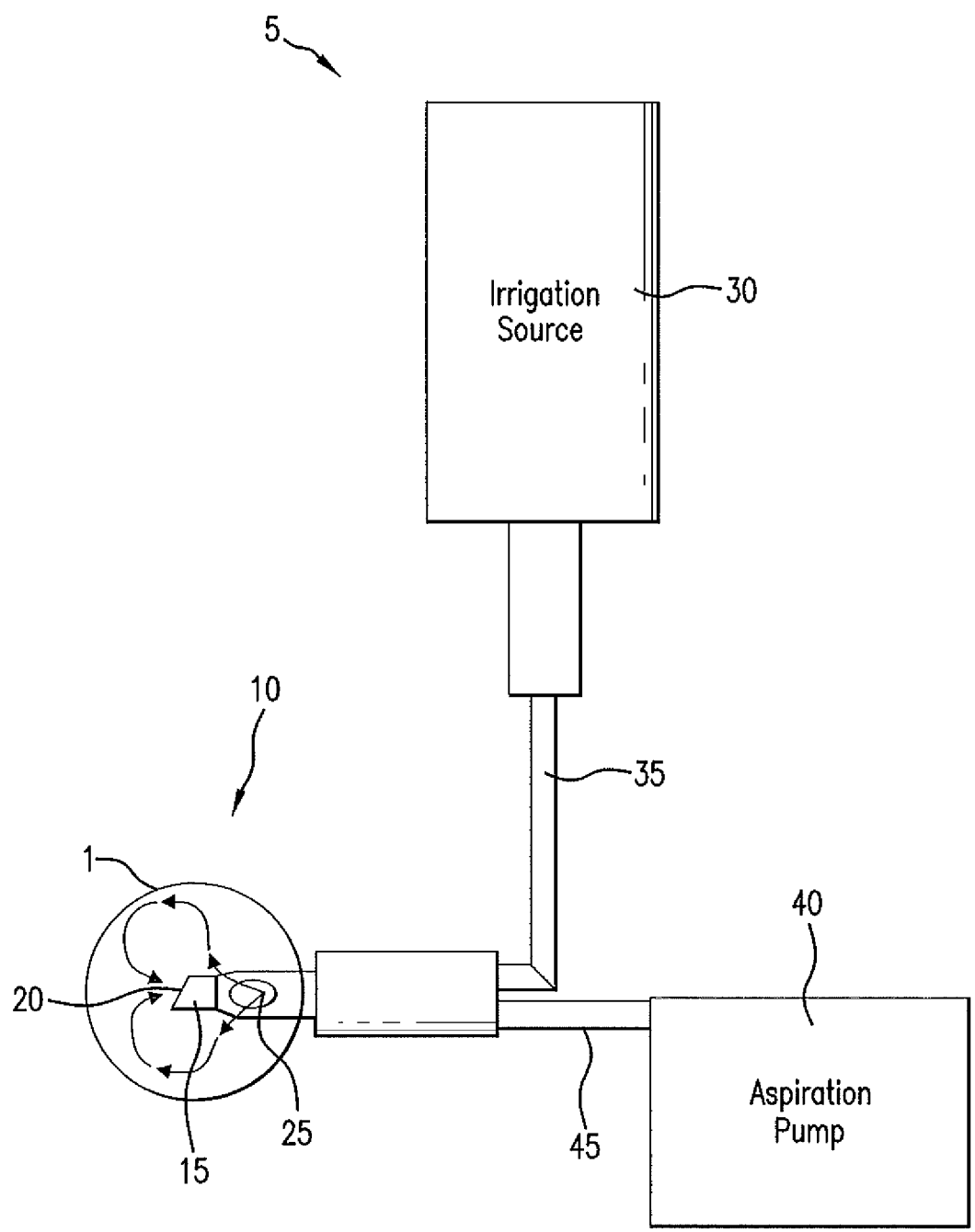
FIG. 1 is a diagram of a phacoemulsification system known in the art.
Figure 4:
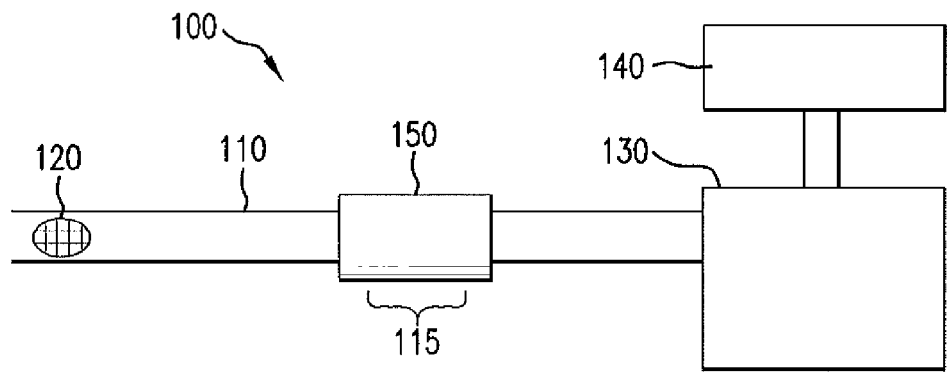
FIG. 4 is a diagram of a vacuum-based aspiration system in accordance with a preferred embodiment.

One approach to address this issue is to utilize a variable flow restrictor. Turning to FIG. 4, a vacuum-based aspiration system 100 having a variable flow restrictor 150 is shown. The variable flow restrictor 150 is located on an aspiration line 110 having an aspiration port 120 at its distal end, and a drainage cassette 130 and vacuum pump 140 at its proximal end. The variable flow restrictor 150 is generally a device, preferably controllable by a computer system (not shown), that variably controls the instantaneous effective resistance of the fluid pathway (e.g., the aspiration line 110) of the system 100. This can allow for precise control of the volumetric flow rate for a vacuum-based pump 140 while still utilizing a wide range of operation. In a preferred embodiment, the variable flow restrictor 150 is configured to deform a specific, localized, deformable segment 115 of the aspiration line 110. By distorting the cross-sectional area of the segment 115 into a smaller total area or by significantly distorting the width vs. height ratio of the segment 115, the instantaneous effective resistance can be increased, which inversely lowers both the current actual volumetric flow rate and also the theoretical maximum volumetric flow rate potential of the fluid.

Figure 5A:
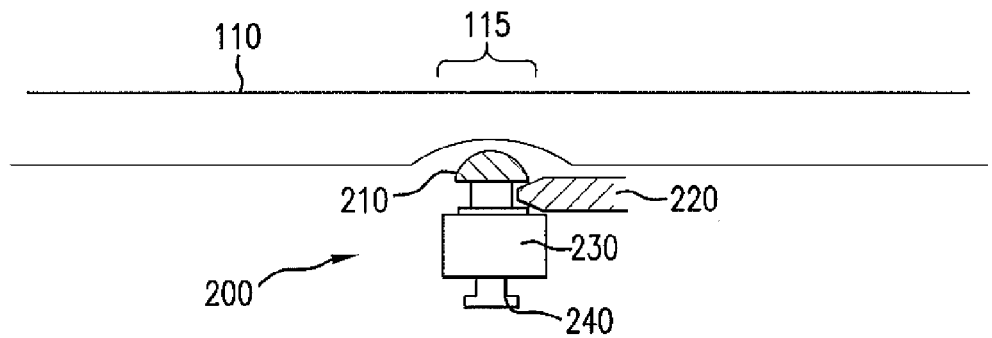
FIG. 5a is a diagram of a variable flow restrictor in accordance with a preferred embodiment.

Turning to FIG. 5a, an example variable flow restrictor 200 is shown in more detail. The segment 115 of the aspiration line 110 coupled to the variable flow restrictor 200 is preferably made of an elastomeric deformable tubing having a resistance variability of at least 2:1 (comparing non-deformed vs. maximum deformation cross-sectional profiles). The variable flow restrictor 200 includes a plunger 210 coupled to an actuator 230 controllable by a computer system (not shown). During operation, the actuator 230 pushes the plunger 210 into mechanical contact with the deformable segment 115 of the aspiration line 110, causing the segment 115 of the aspiration line 110 to deform, thereby adjusting the effective resistance, as explained above. The actuator 230 can be any type of actuator known in the art, such as a mechanical actuator (e.g., a linear motor, axial solenoid, rotary solenoid, or electro magnetic motor), a pneumatic actuator (e.g., such as a low friction pneumatic rotary or axial bladder/cylinder with a variable pressure supply) or a thermal actuator (e.g., such as a bi-metallic strip). A pneumatic actuator is preferable because it can be continuously variable, which desirably increases the resolution of the control of the plunger 210 and thus the control of the effective resistance. In addition, a spacer 220, such as a wedge or cam, (also controllable by a computer system (not shown)), can be utilized in between the plunger 210 and the actuator 230 (or behind the actuator 240) to further control the plunger's 210 range of motion, thereby increasing controllability of the effective resistance.

Figure 5B:
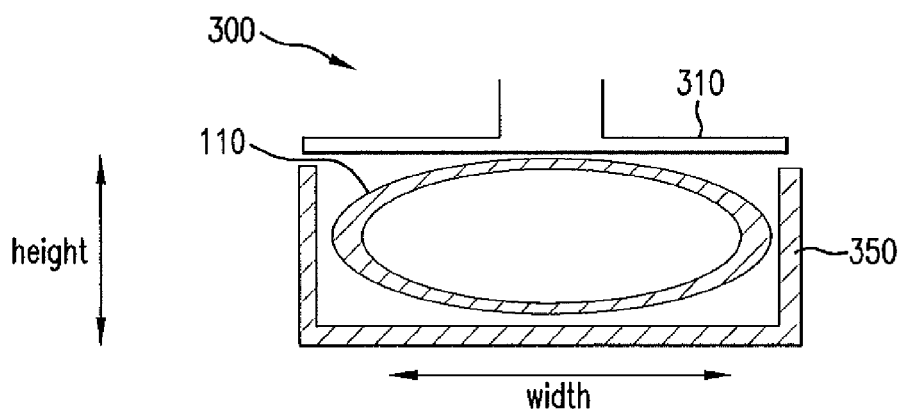
FIG. 5b is a diagram of another variable flow restrictor in accordance with a preferred embodiment.

Turning to FIG. 5b, another variable flow restrictor 300 is shown coupled to the aspiration line 110 (shown in cross-sectional view). This variable flow restrictor 300 includes a rigid case 350, having a fixed height, surrounding the line 110. The case 350 limits the amount of deformation on the line 110. The restrictor 300 further includes a flat plunger 310 having a width greater than the width of the case 350. The plunger 310 is coupled to an actuator (not shown) such as the actuator 230 described above. The actuator pushes the plunger 310 into mechanical contact with the line 110, causing the line 110 to deform; however, deformation of the line 110 is limited to the top of the case 350.

Other variable flow restrictors 150 that deform segment 115 include devices that stretch the segment 115 in the longitudinal direction of the line 110 (not shown) and also devices that twist the segment 115 into a spiral shape (not shown). In addition, the variable flow restrictor 150 can be a device that is integrated with the line 110, for example, a chamber (not shown) within the line 110 with a deformable cross-section.

Flow Rate Sensing Method

Figure 6:
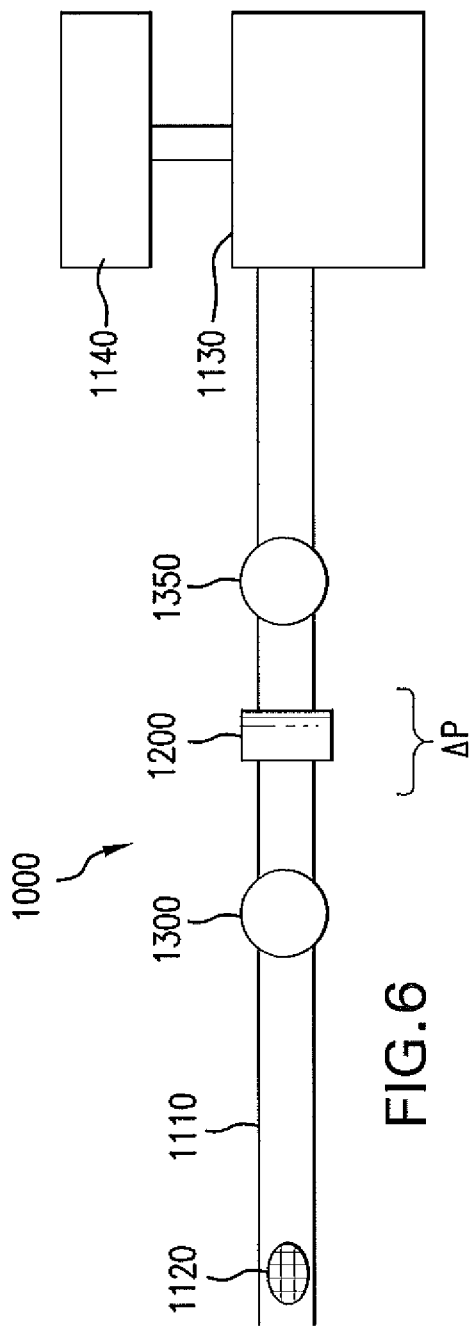
FIG. 6 is a diagram of another vacuum-based aspiration system in accordance with a preferred embodiment.

As mentioned above, with aspiration systems having flow pumps 50 (FIG. 2), if an occlusion occurs, the vacuum level within the aspiration line 45 between the pump 50 and the aspiration port 20 will increase; however, for current systems with vacuum-based pumps 60 (FIG. 3), the vacuum level within the aspiration line 45 is tied to the vacuum generated by the pump 60 and thus, may not be an effective indicator of whether an occlusion has occurred. Turning to FIG. 6, another vacuum-based aspiration system 1000 is shown. The aspiration system 1000 includes a flow restrictor 1200, which is preferably a variable flow restrictor but can be a fixed flow restrictor, located on an aspiration line 1110 having an aspiration port 1120 at its distal end and a drainage cassette 1130 and vacuum-based pump 1140 at its proximal end. Further included are first and second vacuum sensors 1300/1350. The first vacuum sensor 1300 is operatively coupled to the aspiration line 1110 between the port 1120 and the restrictor 1200 ("port 1120 side'), and the second vacuum sensor 1350 is located between the restrictor 1200 and the pump 1140 ("pump 1140 side").

As one of ordinary skill in the art would appreciate, during aspiration, by increasing the effective resistance in a localized segment of the aspiration line 1110, the flow restrictor 1200 will produce a differential volumetric flow rate between the port 1120 side of the line and the pump 1140 side of the line. This accordingly, will cause a vacuum or pressure differential, $\Delta P$, between the port 1120 side of the line 1110 and the pump 1140 side of the line. The vacuum level, or pressure, on the pump 1140 side of the line 1110 will generally be substantially tied to the vacuum level of the pump 1140; however, the vacuum level, or pressure, on the port 1120 side can vary with the volumetric flow rate in the port 1120 side. For example, if an occlusion in the port 1120 occurs, the volumetric flow rate on the port 1120 side of the line will be reduced, which will in turn reduce the pressure, $P_{port\text{-}side}$, on the port 1120 side of the line, while the vacuum, or pressure, $P_{pump\text{-}side}$, on the pump 1140 side of the line remains substantially tied to the vacuum-level of the pump. By utilizing the first and second vacuum sensors 1300/1350, a $\Delta P$ ($P_{port\text{-}side} - P_{pump\text{-}side}$) pressure differential can be measured and utilized in a computer-based algorithm, such as those described in the Claus and Barwick applications referenced above, to detect the onset, presence, breakage, or elimination of an occlusion. If the flow restrictor 1200 is a variable flow restrictor, then the vacuum-based aspiration system 1000 can provide both computer-based detection of occlusion and precise control of the volumetric flow rate while still maintaining the vacuum-based pump's 1140 full range of operation.

Another approach to detect the occurrence of an occlusion is to utilize a Doppler flow meter, known in the art, to measure the volumetric flow rate in the aspiration line (not shown). When an occlusion occurs, the volumetric flow rate will decrease, which will be detected by the Doppler flow meter, and the aspiration system (vacuum or flow pump based) can respond accordingly.

Figure 7:
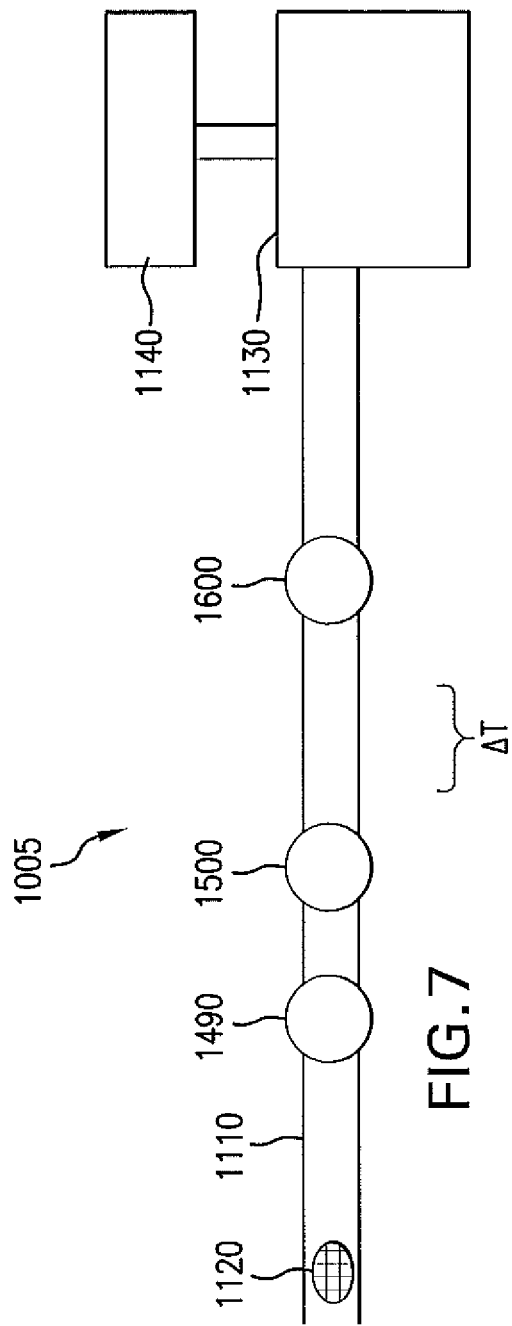
FIG. 7 is a diagram of another vacuum-based aspiration system in accordance with a preferred embodiment.

In yet another approach to detect the occurrence of an occlusion is to utilize a technique known in the art as thermodilution, which is the measurement of rate of fluid flow in a fluid circuit based on the change in temperature of the fluid from one point of the circuit to another downstream. Turning to FIG. 7, another vacuum-based aspiration system 1005 is shown having the same parts as aspiration system 1000 except instead of pressure sensors 1300 and 1350, temperature sensors 1500/1600 are used. In this embodiment, a first temperature sensor 1500 for measuring fluid is coupled to the aspiration line 1110 towards the distal section of the line 1110, and a second temperature sensor 1600 is coupled downstream of the first sensor 1500 towards the proximal section of the line 1110. The change in temperature, $\Delta T$, in the fluid as read by the sensors 1500/1600 will correlate with the rate of fluid flow, as one of ordinary skill in the art would appreciate, e.g., a higher rate of fluid flow will cause a smaller change in temperature compared to a lower rate of fluid flow. In another embodiment (not shown), instead of a first temperature sensor 1500, a fluid of a known starting temperature is injected into the aspiration line 1110. Again, a $\Delta T$ is measured using the second temperature sensor 1600. In yet another embodiment, instead of or in addition to a first temperature sensor 1500, a heating element 1490 is used to heat the fluid within the line 1110 to a desired temperature. Again, $\Delta T$ is measured using the second temperature sensor 1600.

Cataract Removal System

Figure 8:
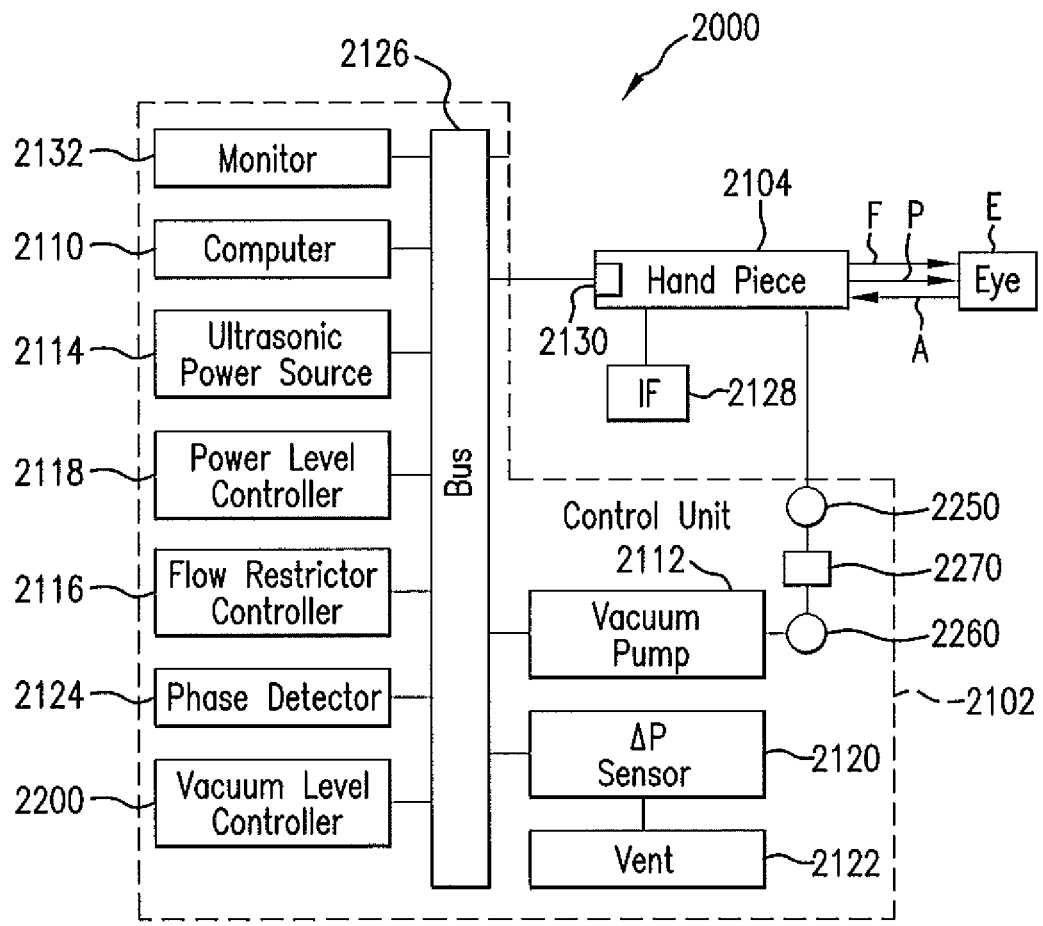
FIG. 8 is a diagram of a phacoemulsification system in accordance with a preferred embodiment.

Turning to FIG. 8, a functional block diagram of a phacoemulsification system in accordance with a preferred embodiment is shown. The system 2000 includes a control unit 2102 and a handpiece 2104 operably coupled together. The handpiece 2104 may include a needle (not shown) for insertion into an eye B and a vibrating unit (not shown) that is configured to ultrasonically vibrate the needle. The vibrating unit, which may include, e.g., a piezoelectric crystal, vibrates the needle according to one or more parameters, such as frequency, pulse width, shape, size, duty cycle, amplitude, and so on. The handpiece 2104 provides power, P, irrigation fluid, F, from an irrigation fluid ("IF") source 2128, and an aspiration line A.

The control unit 2102 includes a vacuum-based pump 2112 operative coupled to aspiration line A, first and second vacuum sensors 2250/2260 in between the pump 2112 and the handpiece 2104, and a flow restrictor 2270 (which is preferably variable) in between the vacuum sensors 2250/2260. The control unit 2102 further includes a microprocessor computer 2110 which is operably connected to and controls the various other elements of the system, such as the vacuum-based pump 2112, a vacuum level controller 2200, a pulsed ultrasonic power source 2114, a flow restrictor controller 2116 (which controls the volumetric flow rate of the aspiration line A by controlling the flow restrictor 2270 as described above), and au ultrasonic power level controller 2118 in accordance with algorithms described in the Claus application referenced above. A pressure differential ΔP sensor 2120 provides an input to the computer 2110 representing the pressure differential between the first and second vacuum sensors 2250/2260. Venting may be provided by a vent 2122. The control unit 2102 may also include a phase detector 2124 for providing an input to the computer 2110 that represents a phase shift between a sine wave representation of the voltage applied to the handpiece 2104 and the resultant current into the handpiece 2104. The functional representation of the system 2000 also includes a system bus 2126 to enable the various elements to be operably in communication with each other.

Dual Pump System

Figure 9:
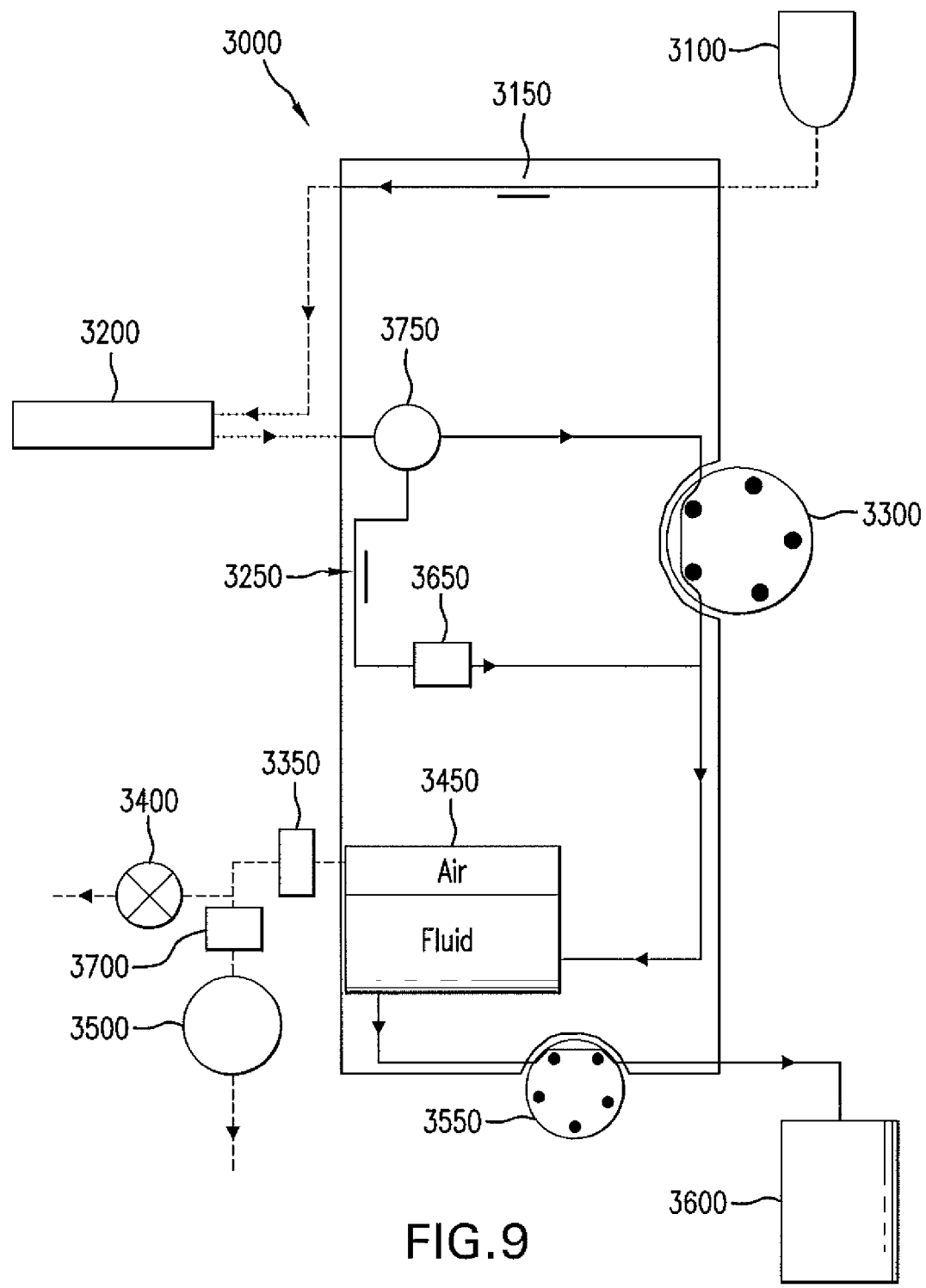
FIG. 9 is a diagram of an irrigation/aspiration system in accordance with a preferred embodiment.

Turning to FIG. 9, an irrigation/aspiration cassette 3000 (preferably disposable) is shown for use in a surgical system, such as a phacoemulsification system. The irrigation/aspiration cassette 3000 includes an irrigation source 3100 operatively coupled to a handpiece 3200 via an irrigation line. An irrigation valve 3150 controls the irrigation source 3100. The handpiece 3200 is further coupled to the aspiration portion of the cassette 3000 having both a vacuum-based pump 3500 and a flow pump 3300. The operation of one or the other is controlled by a selector valve 3250. When the selector valve 3250 is closed, then the flow pump 3300, which is a first peristaltic pump 3300 is the present embodiment, aspirations the fluid from the handpiece 3200. The flow pump 3300 pushes the fluid to a holding tank 3450, which is then drained to a collection bag 3600 by a second peristaltic pump. A vacuum sensor 3750 communicatively coupled to a computer system not shown) is utilized between the flow pump 3300 and the handpiece 3200 to detect any change in vacuum level, which can indicate a possible occlusion.

When the selector valve 3250 is open, then the fluid flows through the circuit controlled by the vacuum-based pump 3500, which creates an air-vacuum in the holding tank 3450 that sucks the fluid from the handpiece 3200. The aspiration portion of the cassette 3000 further includes an air filter 3350 and a vent valve 3400, which are utilized by the flow pump 3300 and the vacuum-based pump 3500. Further included in the circuit controlled by the vacuum-pump 3500 is a flow restrictor 3650 (preferably variable) and an air transducer 3700 operatively located in between the holding tank 3450 and the vacuum pump 3500. The flow restrictor 3650 enables direct control of the volumetric flow rate, as explained above, and the pressure differential, ΔP, can be measured by using both the air-coupled vacuum transducer 3700 and the fluid-coupled vacuum sensor 3750 also used by the flow pump 3300 when in operation. The aspiration/irrigation cassette 3000 shown in FIG. 8 provides the surgeon with a choice between a vacuum-based pump or a flow pump within a single surgical system, such as a phacoemulsification system. Further, the cassette 3000 allows the flow pump 3300 and the vacuum-based pump 3500 to share a common fluid circuit, which can reduce the manufacturing costs and the volume/length of the aspiration pathway is reduced.

In the foregoing specification, the invention has been described with reference to specific embodiments thereof. It will, however, be evident that various modifications and changes may be made thereto without departing from the broader spirit and scope of the invention. For example, the reader is to understand that the specific ordering and combination of process actions described herein is merely illustrative, and the invention may appropriately be performed using different or additional process actions, or a different combination or ordering of process actions. For example, this invention is particularly suited for applications involving medical systems, but can be used beyond medical systems in general. As a further example, each feature of one embodiment can be mixed and matched with other features shown in other embodiments. Additionally and obviously, features may be added or subtracted as desired. Accordingly, the invention is not to be restricted except in light of the attached claims and their equivalents.

What is claimed is:

1. An aspiration system comprising:
   an aspiration line having distal and proximal ends and an aspiration port defined in the distal end;
   a fluid transport device operatively coupled to the proximal end of the aspiration line;
   a variable flow restrictor, the variable flow restrictor operatively coupled to the aspiration line in between the fluid transport device and the aspiration port;
   a first pressure/vacuum sensor operatively coupled to the aspiration line between the port and the variable flow restrictor;
   a second pressure/vacuum sensor configured to measure both pressure and vacuum and operatively coupled to the aspiration line between the variable flow restrictor and the fluid transport device, wherein at least one of the first pressure/vacuum sensor and the second pressure/vacuum sensor is at least partially disposed within a drainage cassette; and
   a computer program product that includes a computer-usable medium having a sequence of instructions which, when executed by a processor, causes said processor to execute a process to measure a differential value equal to a difference in a first pressure/vacuum of the first pressure/vacuum sensor and a second pressure/vacuum of the second pressure/vacuum sensor.

2. The system of claim 1, wherein the aspiration system is configured to be coupled to a phacoemulsification system.

3. The system of claim 1, wherein the fluid transport device is a vacuum based pump.

4. The system of claim 1, wherein one of the first and second pressure/vacuum sensors includes an air transducer.

5. The system of claim 1, wherein the aspiration line includes a deformable segment operatively coupled to the variable flow restrictor, and the variable flow restrictor comprises:
   a plunger element; and
   an actuator coupled to the plunger element and configured to deform the deformable segment via the plunger element.

6. The system of claim 1, further comprising:
   a computer program product that includes a computer-usable medium having a sequence of instructions which, when executed by a processor, causes said processor to control the variable flow restrictor.

7. The system of claim 1, further comprising a controller operatively coupled to the computer program product and configured to:

control a system parameter to be greater than or equal to the lower value or to be less than or equal to an upper value;

sense an occlusion in the aspiration line based on the differential between the first and second pressure/vacuum sensors;

determine a duration of occlusion; and control a system parameter based at least in part on at least one of (2) the sensing of an occlusion and (2) the duration of occlusion.

8. The system of claim 1, further comprising a controller operatively coupled to the computer program product and configured to sense a drop in a controlled system parameter below a lower threshold and, in response to the drop, control the controlled system parameter to be less than or equal to an upper value.

9. The system of claim 1, further comprising a controller operatively coupled to the computer program and configured to sense a rise in a controlled system parameter above an upper threshold and, in response to the rise, control the controlled system parameter to be greater than or equal to a lower value.

* * * * *